United States Patent
Zhang et al.

(10) Patent No.: US 8,551,767 B2
(45) Date of Patent: Oct. 8, 2013

(54) SENSOR FOR DETECTION OF NUCLEIC ACID

(75) Inventors: Guojun Zhang, Singapore (SG); Huiyl Jay Chua, Singapore (SG); Ru Ern Chee, Singapore (SG); Narayanan Bala Subramanian, Singapore (SG); Ross Barnard, Toowong (AU); Uppili Raghavan, Singapore (SG)

(73) Assignees: Agency of Science, Technology and Research, Singapore (SG); BCI (Biochip Innovations) (AU); Simems, Singapore (SG)

( * ) Notice: Subject to any disclaimer, the term of this patent is extended or adjusted under 35 U.S.C. 154(b) by 0 days.

(21) Appl. No.: 13/125,302

(22) PCT Filed: Nov. 20, 2008
(Under 37 CFR 1.47)

(86) PCT No.: PCT/SG2008/000441
§ 371 (c)(1),
(2), (4) Date: Oct. 3, 2011

(87) PCT Pub. No.: WO2010/059126
PCT Pub. Date: May 27, 2010

(65) Prior Publication Data
US 2012/0129709 A1 May 24, 2012

(51) Int. Cl.
| | |
|---|---|
| *C12M 1/34* | (2006.01) |
| *C12M 3/00* | (2006.01) |
| *C12M 1/00* | (2006.01) |
| *C12P 19/34* | (2006.01) |
| *C12Q 1/68* | (2006.01) |
| *C07H 21/02* | (2006.01) |

(52) U.S. Cl.
USPC ..... 435/287.2; 435/6.1; 435/91.1; 435/283.1; 536/23.1; 536/31; 422/430; 977/762; 977/769; 977/938

(58) Field of Classification Search
USPC ........... 435/6.1, 91.1, 283.1, 287.2; 422/430; 536/23.1, 31; 977/762, 769, 938
See application file for complete search history.

(56) References Cited

U.S. PATENT DOCUMENTS

| | | | |
|---|---|---|---|
| 5,378,841 A | 1/1995 | Summerton et al. | |
| 6,391,558 B1 * | 5/2002 | Henkens et al. | 435/6.11 |
| 6,451,588 B1 * | 9/2002 | Egholm et al. | 435/287.2 |
| 2006/0205013 A1 | 9/2006 | Shim et al. | |
| 2010/0035248 A1 * | 2/2010 | Levicky et al. | 435/6 |

OTHER PUBLICATIONS

Mackenzie, Susan, International Search Report, PCT/SG2008/000441, Australian Patent Office, Feb. 3, 2009.
Gao, Z. et al. "Silicon nanowire arrays for label-free detection of DNA," Analytical Chemistry, 2007, pp. 3291-3297, Vo. 79, No. 9.
Li, Z, et al., "Silicon nanowires for sequence-specific DNA sensing: device fabrication and simulation," Applied Physics A: Materials Science & Processing, 2005, pp. 1257-1263, vol. 80, No. 6.

* cited by examiner

*Primary Examiner* — Narayan Bhat
(74) *Attorney, Agent, or Firm* — Joseph R. Baker, Jr.; Gavrilovich, Dodd & Lindsey LLP (57) ABSTRACT

A sensor for detection of target nucleic acid comprising (a) a semiconductor nanostructure; and (b) a nucleic acid detection probe immobilized on the semiconductor nanostructure capable of hybridizing with the target nucleic acid, the detection probe comprising a polymer with a substantially non-ionic backbone.

19 Claims, 3 Drawing Sheets

SENSOR FOR DETECTION OF NUCLEIC ACID

CROSS REFERENCE TO RELATED APPLICATIONS

This application is filed under 35 USC §371 and is based upon International Application No. PCT/SG2008/000441, filed Nov. 20, 2008 and published in English on May 27, 2010, the disclosure of which is incorporated herein by reference in its entirety.

TECHNICAL FIELD

The present invention relates to a sensor for the detection of nucleic acid, such as DNA and RNA. The invention also relates to a method of detecting nucleic acid and to a system and kit for detecting nucleic acid.

BACKGROUND

DNA microarrays used as gene chips are high-throughput devices used to determine the expression profiles of many genes simultaneously. DNA microarrays are used in the fields of molecular biology and medicine for basic research, disease diagnostics and drug discovery. The basis of microarray detection is the ability of a given nucleic acid target molecule to bind specifically to, or hybridize with, a nuclear acid probe having a complementary nucleic acid via Watson/Crick base pairing. In microarrays, nucleic acid probes, each being complementary to a particular target nucleic acid encoding particular information, are immobilized in an arrayed manner to a specific designated position on a substrate. The presence of a target nucleic acid in a sample will result in the hybridization of the target nucleic acid with the immobilized nucleic acid probe, which has a complementary nucleic acid sequence to the target nucleic acid. As the specificity of nucleic acid hybridization is highly dependent on the level of complementary bases between the probes and target nucleic acids, detection of a specific target nucleic acid requires the immobilization of the specific probe, which is optimal for the capture of the target nucleic acids. Hybridization conditions such as buffer, temperature and incubation time can also affect the specificity of the hybridization. Hence, depending on stringency of the hybridizing conditions, probes can bind to target nucleic acids that are less than 100% complementary. Thus to ensure optimal hybridization, hybridization conditions need to be tailored to individual sets of DNA probes.

In known microarray detection systems, the detection of a successful hybridization is usually undertaken optically by the detection of fluorescence from the sample nucleic acids, which have been pre-labeled with a fluorophore bound to the immobilized nucleic acid probe. However, a rather complex laser optical detection system is required for detection of the fluorescence, which is a major drawback.

DNA microarray chips are generally considered as a single use product. However, some DNA microarray chips have been be re-used although their stability does decrease with reuse. To reuse a microarray, the arrays can be treated with heat or base-pH treatment to denature the duplex between the probe and target nucleic acid. The stripped array can then be reused for another re-hybridization with sample nucleic acids. Unfortunately, depending on the type of surface attachment used to immobilize the probe, the signal generally reduces by about 30%-50% after three or more rounds of stripping and re-hybridization.

Once the probes have been spotted to the array chip, the information that can be derived from the chip is limited only to the information that the immobilized probes are meant to capture. For example, DNA arrays used for detection of insulin expression cannot be used for detection of actin expression. This limited reusability of the DNA microarray chip, inflexibility of probe spotted array chips and expensive detection equipment gives rise to high costs for using microarrays, especially in the diagnostic sector where a large number of samples need to be tested.

With the development of microelectronic technology, the use of semiconductor technology in DNA microarrays has been utilized. Instead of measuring fluoresence intensity, changes in electrical current may be used to detect or "readout" successful hybridization. Use of semi-conductor technology for DNA microarrays requires the immobilization of the nucleic acid probe to the silicon surface of a field effect transistor (FET). Hybridization of target nucleic acid with a nucleic acid probe elicits a change in resistance, and in turn the current flowing through the FET, which constitutes the basis of the readout of the microarray assay. However, because of the relatively weak donating and withdrawing effects of small charged nucleic acids, a sufficient amount of hybridization between sample nucleic acids and probes is required to induce a measurable resistance change. The use of silicon nanowire (SiNW) as the surface for nucleic acid immobilization helps negate this former problem.

SiNW are silicon wires with diameters constrained to tens of nanometers or less and which exhibit unique properties such as super conductance. SiNW are ultra-sensitive FET biosensors that allow a small localization of charge to become a significant gate to the flow of current in the FET.

DNA has been used in nucleic acid probes for capture of target nucleic acids in microarrays. However, DNA, being negatively charged, does suffer from drawbacks when used in nucleic acid probes for SiNW arrays. This is because the natural negative charges of the DNA probes results in the formation of a densely charged layer at the surface of the silicon substrate which in turn induces a strong electrical field at the SiNW surface. This in turn increases the background noise of the baseline signal generated by the SiNW. Therefore, to induce significant charge variation in the SiNW FET, a significant amount of target nucleic acids are required to be bound to the DNA probes in order to overcome the high noise baseline. This makes the detection of small amounts of target nucleic acids difficult. DNA, being a natural polymer, is also easily degraded by enzymes found in the samples or the environment. This in turn reduces the reusability of the SiNW biosensor.

Therefore, there is a need to provide a sensor, which overcomes, or at least ameliorates, one or more of the disadvantages described above.

SUMMARY

According to a first aspect, there is provided a sensor for detection of target nucleic acid comprising:
  a semiconductor nanostructure; and
  a nucleic acid detection probe immobilized on said semiconductor nanostructure capable of hybridizing with said target nucleic acid, said detection probe comprising a polymer with a substantially non-ionic backbone.

According to a second aspect, there is provided a sensor for detection of target nucleic acid comprising:
  a semiconductor nanostructure; and
  a nucleic acid detection probe immobilized on said semiconductor nanostructure capable of hybridizing with said target nucleic acid, said detection probe comprising a polymer with a substantially non-ionic backbone with the proviso that peptide nucleic acid (PNA) is excluded.

Advantageously, the semiconductor nanostructure may be configured to form a gate insulator of an electric field transistor to induce changes in an electric field when the target nucleic acid hybridizes with the polymer.

The polymer of the nucleic acid detection probe may have a target sequence moiety for hybridizing to a target nucleic acid. The target sequence moiety may be a sequence of defined nucleic acid bases that are complementary to the sequence of the target nucleic acid. Advantageously, due to the complementary base pairing of the target sequence moiety with the target nucleic acid, the sensor may have a high affinity and selectivity for the target nucleic acid.

The nucleic acid detection probe may be covalently attached onto the semiconductor nanostructure. Advantageously, due to the strong covalent bonding between the nucleic acid detection probe and the semiconductor nanostructure, the sensor can be re-used without any substantial loss in the ability of the nucleic acid detection probe to re-hybridize with a target nucleic acid after denaturing from target nucleic acid.

Advantageously, the use of a polymer with a substantially non-ionic backbone as the nucleic acid detection probe may result in minimal background noise during target nucleic acid detection due to the non-ionic charge of the polymer.

According to a third aspect, there is provided a sensor for detection of target nucleic acid comprising:

a semiconductor nanostructure; and a nucleic acid detection probe immobilized on said semiconductor nanostructure capable of hybridizing with said target nucleic acid, said detection probe comprising a first polymer having a substantially non-ionic backbone and a binding moiety that binds to a binding moiety of a second polymer, said second polymer having a substantially non-ionic backbone and having a target sequence moiety that is capable of hybridizing with said target nucleic acid.

Advantageously, the target sequence moiety of the second polymer may be selected to target a specific target nucleic acid. This allows the possibility of tailoring the specificity of the second polymer to target a particular target nucleic acid.

Furthermore, the second polymer can be replaced with another type of second polymer that is specific for a different nucleic acid sequence.

In one embodiment, the second polymer is not immobilized to the semiconductor nanostructure and hence the second polymer when denatured from the first polymer can be replaced by another second polymer having a different target sequence moiety. Hence, due to the possibility of replacing or changing the target sequence moiety of the second polymer, different types of nucleic acid with different sequences can bind to the respective second polymers. This leads to an increase in the flexibility of the sensor such that different types of nucleic acids can bind to the sensor.

According to a fourth aspect, there is provided a nucleic acid microarray sensor for detection of plural target nucleic acid sequences comprising:

a semiconductor nanostructure; and an array of nucleic acid detection probes immobilized on said semiconductor nanostructure capable of hybridizing with said target nucleic acid sequences, each detection probe comprising:

a first polymer having a substantially non-ionic backbone and a binding moiety that binds to a binding moiety of a second polymer, said second polymer having a substantially non-ionic backbone and having a target sequence moiety that is capable of hybridizing with said nucleic acid;

wherein different nucleic acid detection probes of said array are configured to hybridize with specific nucleic acid sequences to thereby differentiate between said plural nucleic acid sequences.

Advantageously, the ability to differentiate between said plural nucleic acid sequences is because of the different target sequence moieties of the second polymer of the array of detection probes. More advantageously, nucleic acids having different sequences can be detected by the nucleic acid microarray sensor.

According to a fifth aspect, there is provided a system for detection of target nucleic acid comprising:

a semiconductor nanostructure;

a nucleic acid detection probe immobilized on said semiconductor nanostructure capable of hybridizing with said target nucleic acid, said detection probe comprising a first polymer having a substantially non-ionic backbone and a binding moiety;

a second polymer with a substantially non-ionic backbone, a binding moiety selected to bind to said binding moiety of said first polymer and a target sequence moiety that is capable of hybridizing with said target nucleic acid; and means for detecting the hybridization between said target nucleic acid and said detection probe.

According to a sixth aspect, there is provided a method for detection of target nucleic acid comprising the steps of:

(a) providing a semiconductor nanostructure and a nucleic acid detection probe immobilized on said semiconductor nanostructure, said nucleic acid detection probe comprising a first polymer having a substantially non-ionic backbone and a binding moiety;

(b) providing a second polymer having a substantially non-ionic backbone, a binding moiety that is capable of binding with said binding moiety of said first polymer and a target sequence moiety that is capable of hybridizing with said target nucleic acid;

(c) hybridizing said target nucleic acid to said target sequence moiety;

(d) allowing said first and second polymer binding moieties to bind to each other before or after said hybridizing step (c); and (e) detecting an electromagnetic field change in said semiconductor nanostructure that is indicative of hybridizing between said target nucleic acid and said target sequence moiety.

Advantageously, the first polymer can be covalently attached to the semiconductor nanostructure. In one embodiment, the semiconductor is a silicon nanostructure that has been functionalized with an amine to confer amine functionality to the surface of the silicon nanostructure. A cross-linker may then be used to bind the amine group attached to the silicon nanostructure to the first polymer. Accordingly, because the first polymer is not coupled to the silicon nanostructure by an oxygen atom (hereafter "oxide-free" coupling), the sensor may have improved detection sensitivity when the target nucleic acid binds to the nucleic acid detection probe.

The method may further comprise the step of blocking the unreacted or exposed surface of the semiconductor nanostructure that does not have a detection probe attached thereon. Advantageously, this may prevent non-specific hybridizing between the target nucleic acid and the semiconductor nanostructure.

According to a seventh aspect, there is provided a kit for detection of target nucleic acid comprising:

a semiconductor nanostructure;

a nucleic acid detection probe immobilized on said semiconductor nanostructure capable of hybridizing with said target nucleic acid, said detection probe comprising a polymer with a substantially non-ionic backbone; and means for detecting the hybridization between said target nucleic acid and said detection probe.

DEFINITIONS

The following words and terms used herein shall have the meaning indicated:

The term "target nucleic acid" as used herein means and includes any nucleic acid or gene the quantification, quantitative determination, qualitative detection, or mere detection of which is intended, irrespective whether it is in a purified form or not and further irrespective of its concentration. Nucleic acids other than the target nucleic acid may also coexist with the target nucleic acid. An assay system may contain one or more types of target nucleic acids. The target nucleic acid may be, for example, at least one specific nucleic acid to be determined in a co-cultivation system of microorganisms (a mixed system containing RNAs or genetic DNAs of plural microorganisms) or in a symbiotic cultivation system of microorganisms (a mixed system containing RNAs or genetic DNAs of plural animals or plants and/or of plural microorganisms). The target nucleic acid can be purified, if needed, according to a conventionally known method. For example, it can be purified using a commercially available purification kit. Examples of the nucleic acids include DNAs, RNAs and chemically modified products of these nucleic acids. Target nucleic acids can range from as few as about 20-30 nt to as many as millions of nucleotides (nt) or basepairs (bp), depending on the particular application.

The terms "nucleic acid probe", "nucleic acid detection probe" and "probe" are to be used inter-changeably and refer to a compound having at least one moiety, which is capable of hybridizing to a target nucleic acid of interest.

The term "moiety" is defined as a portion of a complete structure of a polymer that includes functional groups and/or discreet bonded residues that are present in the macromolecule of a polymer. For example, a "binding moiety" refers to those parts of the polymer which have the function of "binding" to other polymers such as, for example, a combination of nucleic acid bases that respectively form the side chains of the polymer, these nucleic acid bases being specifically arranged to promote binding between two polymers via complementary base pairing. A "target sequence moiety" refers to that part of the polymer, which comprises nucleic acid bases that respectively form the side chains of the polymer, these nucleic acid bases being specifically arranged to thereby hybridize to a target nucleic acid having complementary base pairs thereon.

The term "non-ionic backbone", when referring to a polymer, is to be interpreted broadly to include any polymer that does not have any substantially charged moieties along the polymer backbone. In embodiments where the polymer refers to Morpholino, the non-ionic backbone comprises repeating morpholine rings linked by phosphorodiamidate bonds. In other embodiments where the polymer refers to PNA, the non-ionic backbone comprises repeating N-(2-aminoethyl)-glycine units linked by peptide bonds.

The term "complementary" refers to the precise paring of purine and pyrimidine bases between two single strands of DNA, and sometimes RNA. As is known in the art, complementary base pairing refers to the binding between adenine (A) and thymine (T) (or Uracil (U), in the case of RNA), as well as between guanine (G) and cytosine (C).

As used herein, the term "hybridization" refers to the process in which two single-stranded polynucleotides bind non-covalently to form a stable double-stranded polynucleotide. The resulting double-stranded polynucleotide is a "hybrid." Hybridization conditions will typically include salt concentrations of less than about 1M, more usually less than about 500 mM and less than about 200 mM. Hybridization temperatures can be as is low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different under different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the thermal melting point (Tm) for the specific sequence at a defined ionic strength and pH. The Tm is the temperature (under defined ionic strength, pH and nucleic acid composition) at which 50% of the probes complementary to the target sequence hybridize to the target sequence at equilibrium. Typically, stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" 2nd Ed. Cold Spring Harbor Press (1989) and Anderson "Nucleic Acid Hybridization" 1st Ed., BIOS Scientific Publishers Limited (1999), which are hereby incorporated by reference in their entireties for all purposes above.

The terms "sensor" and "biosensor" are to be used interchangeably and are to be interpreted broadly to refer to an analytical device that is capable of converting a biological response into an electrical signal. The sensor or biosensor is capable of registering a change in an electrical property when a target nucleic acid binds or hybridizes to a nucleic acid detection probe immobilized on the surface of a semiconductor nanostructure making up the sensor or biosensor.

The terms "gene chip" and related term "microarray", are to be interpreted broadly to refer to a device that comprises the sensor disclosed herein together with auxiliary components such as electrical source and electrodes for conducting electricity through the gene chip such that a change in the electric field is indicative of hybridization between target nucleic acid and the nucleic acid detection probe. The gene chip may further require a use of an electrical detector for detecting this change in the electric field. This "change in the electric field" can be seen as the presence of an electric field though the gene chip as the target nucleic acid binds to the nucleic acid detection probe or can be seen as a decrease in the electric field due to increased electrical resistance that occurs due to hybridization of the target nucleic acid to the nucleic acid detection probe.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Disclosure of Optional Embodiments

Exemplary, non-limiting embodiments of a sensor for detection of nucleic acid will now be disclosed. The sensor comprises a semiconductor nanostructure and a nucleic acid detection probe immobilized on the nanostructure that is capable of hybridizing with target nucleic acid, the detection probe comprising a polymer with a substantially non-ionic backbone.

In one embodiment, the polymer comprises a non-ionic backbone with the proviso that peptide nucleic acid (PNA) is excluded. The polymer of the nucleic acid detection probe excludes DNA and RNA. The polymer of the nucleic acid detection probe may exclude non-ionic analogs of nucleic acid. In another embodiment, the polymer of the nucleic acid detection probe may be peptide nucleic acid (PNA). The PNA may have the structure as shown below.

PNA

As can be seen in the above structure of PNA, the backbone is made up of repeating N-(2-aminoethyl)-glycine linked by peptide bond.

In a further embodiment, the polymer of the nucleic acid detection probe may be a morpholino oligomer. The morpholino oligomer may have the structure as shown below.

Morpholino

The morpholino backbone is made up of repeating ribonucleoside derived morpholine subunits linked by phosphorodiamidate bond. Morpholino oligomers may be short chains of about 25 morpholine subunits. Each morpholino subunit is made up of a nucleic acid base, a morpholine ring and a non-ionic phosphodiamidate intersubunit linkage. Morpholinos and its subunits used is in their assembly are covered by U.S. Pat. Nos. 5,142,047 and 5,185,444, herein incorporated by reference in its entirety, which also disclose methods for imparting specific target sequence moieties ("base pairing moieties") to the Morpholino.

The polymer of the nucleic acid detection probe may have a target sequence moiety for hybridizing to a target nucleic acid. The target sequence moiety may be a sequence of defined nucleic acid bases that are complementary to the sequence of the target nucleic acid. The nucleic acid bases include purine such as cytosine and guanidine as well as pyrimidine such as adenine and thymine. Due to the complementary base pairing of the target sequence moiety with the target nucleic acid, the sensor may have high affinity and selectivity for the target nucleic acid.

The semiconductor nanostructure may be a semiconductor selected from Group IIIA, IVA, VA or VIA of the Periodic Table of Elements. The semiconductor may be selected from the group consisting of silicon, germanium, tin, selenium, tellurium, boron, carbon, diamond carbon and phosphorous.

The semiconductor nanostructure may be a Group IVA-Group IVA semiconductor, a Group IIIA-Group VA semiconductor, a Group IIB-Group VIA semiconductor, a Group IIA-Group VIA semiconductor, a Group IVA-Group VIA semiconductor, a Group IB-VIIA semiconductor, alloys or combinations thereof. The semiconductor may be selected from the group consisting of SiC, BN, BP, Bas, AlN, AlP, AlAs, AlSb, GaN, GaP, GaAs, GaSb, InN, InP, InAs, InSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, AgF, AgCl, AgBr, AgI, alloys or combinations thereof.

The semiconductor may be suitably doped to form a p-type semiconductor or a n-type semiconductor. It is to be appreciated that a person skilled in the art would know the type of dopants to use in order to form the p-type or n-type semiconductor.

The semiconductor nanostructure may be a semiconductor nanowire, a semiconductor nanotube or a semiconductor nanorod. In one embodiment, the semiconductor nanowire is a silicon nanowire. In another embodiment, the semiconductor nanotube is a carbon nanotube.

In embodiments where a semiconductor nanowire is used, the diameter of the nanowire may be selected from the group consisting of about 30 nm to about 100 nm, about 50 nm to about 100 nm, about 70 nm to about 90 nm, about 30 nm to about 50 nm, about 30 nm to about 70 nm, about 30 nm to about 90 nm, about 50 nm to about 70 nm and about 60 nm to about 70 nm. In one embodiment, the diameter of the nanowire is about 50 nm to 60 nm.

The length of the nanowire may be selected from the group consisting of about 1 µm to about 250 µm, about 1 µm to about 200 µm, about 1 µm to about 150 µm, about 1 µm to about 100 µm, about 1 µm to about 50 µm, about 50 µm to about 250 µm, about 50 µm to about 200 µm, about 50 µm to about 150 µm, about 50 µm to about 100 µm, about 100 µm to about 250 µm, about 150 µm to about 250 µm, about 200 µm to about 250 µm, about 100 µm to about 150 µm, about 150 µm to about 200 µm. In one embodiment, the length of the nanowire is about 100 µm to about 200 µm. The sensor may comprise an array of more than one semiconductor nanostructure. The sensor may have at least 100 nanowires positioned in an array format.

The nucleic acid detection probe may be attached or immobilized onto the semiconductor nanostructure via a cross-linker. The nucleic acid detection probe may be covalently attached to the semiconductor nanostructure. The cross-linker may be an organic compound that may be capable of covalently binding the polymer to the semiconductor nanostructure. The cross-linker may be an organic compound whereby both of the terminal ends are of an oxo (that is, —C=O) group. The cross-linker may be a dialdehyde or a diisocyanate group. The cross-linker may be glutaraldehyde or phenylene diisocyanate.

The semiconductor nanostructure may be treated to promote binding of the cross-linker to the semiconductor nanostructure. This may be achieved by introducing a functionalizing agent such as an amino-group containing compound. The amino-group containing compound may be an aminoalkene having from 2 to 15 carbon atoms. Exemplary aminoalkene may be selected from the group consisting of aminoethene, aminopropene, aminobutene, aminopentene, aminohexene, aminoheptene, aminooctene, aminononene, aminodecene, aminoundecene, aminododecene, aminotridecene, aminotetradecene and aminopentadecene. In one embodiment, the functionalizing agent may be 10-aminodec-1-ene. The functionalizing agent may be protected with a protecting group so as to prevent undesired reaction of the amino group. Accordingly, the functionalizing agent may be 10-N-Boc-aminodec-1-ene. The amino-group containing compound may be aminopropylethoxysilane or polylysine.

The nucleic acid detection probe may be attached or immobilized onto the semiconductor nanostructure via affinity binding. In affinity binding, compounds are linked to each other or to a surface of an article through specific biological binding (e.g. biotin/streptavidin or glutathione/glutathione-S-transfersase). In one embodiment, this is achieved by chemically modifying the nucleic acid detection probe to contain biotin and the semiconductor nanostructure surface to contain streptavidin. Application of the biotin-modified nucleic acid probe to the streptavidin-modified surface will result in specific affinity immobilization of the nucleic acid probe to the semiconductor surface.

After the nucleic acid detection probe has been immobilized onto the semiconductor nanostructure, the non-exposed surface of the semiconductor nanostructure may be blocked in order to reduce non-specific hybridization between the nucleic acid and the semiconductor nanostructure. The blocking agent used is not particularly limited as long as it is capable of blocking the hybridization of the nucleic acid to the semiconductor nanostructure. An exemplary blocking agent may be serum or bovine serum albumin.

The type of nucleic acid that can be detected by the disclosed sensor may be single stranded DNA and/or single stranded RNA. Optionally, the target nucleic acid may be labeled with a fluorescent marker or a radioactive marker such that any nucleic acid that has been bound to the nucleic acid detection probe can be detected using fluorescence imaging or radiation, respectively.

In one embodiment, the nucleic acid detection probe may comprise a first polymer and a second polymer. The first and second polymer may have respective binding moieties with respective substantially non-ionic backbones. The binding moieties of the first and second polymer may bind to each other as a result of complementary base-pairing based on the specific sequence of the nucleic acid bases present in the respective binding moieties.

The second polymer may have a binding moiety as described above at one end and a target sequence moiety for hybridization to a target nucleic acid at the other end. Similar to that described above, the target sequence moiety of the second polymer may comprise a sequence of defined nucleic acid bases that are complementary to the sequence of the target nucleic acid.

The second polymer may have a different number of monomer units relative to that of the first polymer. The second polymer may have more monomer units than those in the first polymer such that the second polymer is capable of binding to both the first polymer and hybridize with the target nucleic acid. The second polymer may have lesser monomer units than those in the first polymer and is capable of binding to both the first polymer and hybridize with the target nucleic acid. The second polymer may have the same number of monomer units as compared to that of the first polymer. The second polymer may at least bind to a portion of the first polymer. The second polymer may at least bind to a portion of the target nucleic acid.

The length of the first polymer may be selected from the group consisting of about 10 to about 30 nucleotides, about 15 to about 25 nucleotides, about 17 to about 25 nucleotides, about 20 to about 25 nucleotides, about 23 to about 25 nucleotides, about 15 to about 23 nucleotides, about 15 to about 20 nucleotides, about 15 to about 17 nucleotides, about 18 to about 23 nucleotides and about 20 to about 23 nucleotides. The length of the second polymer may be selected from the group consisting of about 25 to about 55 nucleotides, about 30 to about 50 nucleotides, about 35 to about 50 nucleotides, about 40 to about 50 nucleotides, about 45 to about 50 nucleotides, about 30 to about 45 nucleotides, about 30 to about 40 nucleotides, about 30 to about 35 nucleotides, about 35 to about 40 nucleotides and about 35 to about 45 nucleotides.

In one embodiment, there is provided a system for detection of target nucleic acid using the sensor as described in the embodiment above and which further comprises means for detecting the hybridization between said target nucleic acid and said detection probe. The means for detecting the hybridization between said target nucleic acid and said detection probe may be any one of a known detection system for detecting hybridization between the target nucleic acid and the detection probe, such as for example, a fluorescence reader, a ammeter, a voltmeter and an ohm meter. In one embodiment, in use, the resistance of the sensor is measured by two terminal electrodes. As the nucleic acid target binds to the target binding moiety of the polymer (in an embodiment where only one polymer is used) or to the target binding moiety of the second polymer (in an embodiment where both a first polymer and second polymer are used), the presence of the negatively-charged nucleic acid molecule results in an increase in the resistance between the two terminal electrodes. Hence, the means for detection is the measurement of this resistance change before and after hybridization, which is indicative of hybridization between the nucleic acid target and the polymer.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 3a is the fluorescence image after the morpholinos have hybridized with one or more target nucleic acids that had been labelled with a Cy-3 fluorescent marker. FIG. 3b is the fluorescence image after the target nucleic acids of FIG. 3a have been denatured and hence removed from the morpholinos.

DETAILED DESCRIPTION OF INVENTION

Figure 1:
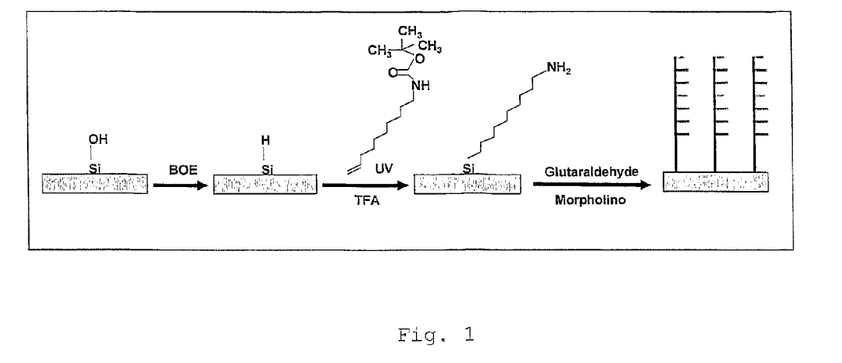
FIG. 1 is a schematic diagram of the process involved in immobilizing a polymer, such as morpholino, onto the surface of a semiconductor nanostructure.

Referring to FIG. 1, there is shown a schematic diagram of the process involved in immobilizing a polymer such as morpholino into the surface of a semiconductor nanostructure. This process is carried out in the absence of an oxide film on the surface of the semiconductor nanostructure. Hence, this process can be termed as an "oxide-free" process. In this process, morpholino is immobilized onto the surface of a silicon nanostructure. The process involves the steps of functionalizing the silicon surface with a functionalizing agent such as an amine-containing compound; covalently attaching one terminal end of a cross-linker to the exposed amine group of the functionalizing agent; and covalently attaching the morpholino to the exposed terminal end of the cross-linker.

In the functionalizing step, the silicon oxide coating of the silicon nanostructure is etched away by exposing the silicon nanostructure to BOE (a solution containing high concentration of HF acid) such that the silicon atoms present on the silicon surface form hydrogen-terminated silicon. The hydrogen-terminated silicon is subsequently and almost immediately treated with 10-aminodec-1-ene functionalizing agent by covering the hydrogen-terminated silicon with a thin film of t-BOC protected 10-aminodec-1-ene and quickly transferring it to a nitrogen-purged Teflon reaction cell. In the reaction cell, the silicon nanostructures are illuminated with UV light. After UV illumination, the silicon nanostructures are rinsed and washed. After washing, the silicon nanostructure was treated to remove the protecting group from the functionalizing agent and to expose the amine group. Due to the presence of the exposed amine group, a cross-linker such as glutaraldehyde can bind to the functionalizing agent. The other end of the cross-linker is exposed to bind to the first polymer such as a morpholino.

Figure 2:
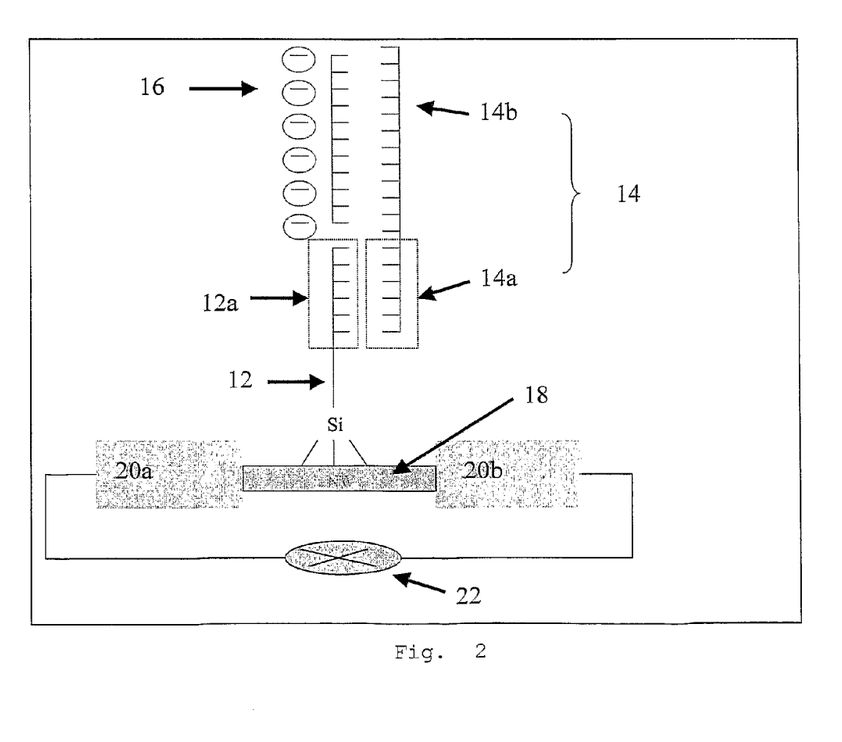
FIG. 2 is a schematic diagram of a first and second polymer immobilized on a semiconductor nanostructure, the second polymer being attached to the first polymer and hybridized to the target nucleic acid.

Referring to FIG. 2, there is shown a schematic diagram of a first polymer such as morpholino 12 and a second polymer such as morpholino 14 immobilized on a semiconductor nanostructure such as silicon nanowire 18. Morpholino 14 is attached to the morpholino 12 and hybridized to a target nucleic acid 16. As seen in FIG. 2, morpholino 12 is capable of binding to morpholino 14 due to the presence of binding moieties on both morpholino 12 and morpholino 14. The binding moieties of morpholino and morpholino 14 are depicted in FIG. 2 by dotted rectangles and represented by 12a and 14a, respectively. The binding moieties (12a, 14a) have defined nucleic acid sequences that are complementary to each other such that morpholino 12 and morpholino 14 bind to each other via complemetary base pairing. In morpholino 14, the target sequence moiety 14b has a specific nucleic acid sequence that is complementary to the nucleic acid sequence of target nucleic acid 16 such that morpholino 14 and target nucleic acid 16 hybridizes with each other via complementary base pairing.

In use, as the target nucleic acid 16 hybridizes with the morpholino 14, a change in the electrical current between electrodes (20a, 20b) can be detected by the detector 22. In some embodiments, the hybridization of the target nucleic acid 16 to the morpholino 14 closes the electrical circuit between electrodes (20a, 20b) such that an electric current can flow between the electrodes (20a, 20b). This is attributed to the negatively charged nucleic acid, which closes the electrical circuit between the electrodes (20a, 20b). The presence of an electric is current can be detected using a detector 22 which may be in the form of a voltmeter or an ammeter. In other embodiments, an electrical current is generated between electrodes (20a, 20b) before introduction of the target nucleic acid 16. Once the target nucleic acid 16 binds to morpholino 14, the negatively charged nucleic acid 16 acts as a resistance to the electrical flow between the electrodes (20a, 20b). Hence, the electrical current between the electrodes (20a, 20b) before and after hybridization of the target nucleic acid 16 to the morpholino 14 can be detected by the detector 22, such as an ammeter or an ohm meter. The magnitude of the change in the electrical current before and after hybridization can be related to the amount of hybridized nucleic acid 16 to morpholino 14.

The target nucleic acid 16 can be labelled with a fluorescent marker (not shown in FIG. 2) such that the hybridized nucleic acid can be detected via fluorescent imaging.

EXAMPLES

Non-limiting examples of the invention will be further described in greater detail by reference to specific Examples, which should not be construed as in any way limiting the scope of the invention.

Example 1

In order to immobilize morpholino to a silicon nanostructure (Hitachi High Technologies (Singapore) Pte. Ltd), a native oxide on the Si (100) surface was etched away by exposing the silicon nanostructure to BOE (Ammonium Fluoride Etchant 6:1 Merck Electron. Chem. Ltd) for 1 min. The H-terminated silicon nanostructures were immediately covered with a thin film of t-BOC protected amine (AstaTech Inc. (Bristol, Pa.)) and quickly transferred to a $N_2$-purged Teflon® reaction cell where the nanostructures were illuminated with UV light (254 nm) for 3 hours through a quartz window. The nanostructures were then rinsed in chloroform (Sigma-Aldrich) for 15 minutes at 50° C. and then in methanol (Sigma-Aldrich) twice at room temperature (such as 25° C.) for 5 minutes each. The deprotection of t-BOC protected amine was carried out by immersing the nanostructure surface in 25% trifluoroacetic acid (TFA) (Sigma-Aldrich) in methylene chloride (Sigma-Aldrich) for 2 hours and subsequently treating the nanostructure surface with 10% aqueous ammonium hydroxide (Sigma-Aldrich) for 5 minutes followed by a rinse in pure $H_2O$. The nanostructures were treated with 1% glutaraldehyde (Sigma-Aldrich) in $H_2O$ for 1 hour and rinsed with pure $H_2O$ thereafter. 10 µM morpholino (each having a base sequence of 5'-$NH_2$-AACCACACAACCTAC-TACCTCA-3' (SEQ ID NO:1)) (Gene Tools, LLC (Philomath, Oreg., USA)) in 1× Saline-Sodium Citrate (SSC) buffer was incubated with the surface in a humid atmosphere at room temperature overnight. After immobilization of the morpholino, the chips were washed three times with 1×SSC buffer for 5 minutes during each wash. 1% bovine serum albumin (BSA) (Sigma-Aldrich) in phosphate buffer saline (PBS) was employed to block the aldehyde-activated surface outside the morpholino spot.

Example 2

Figure 3A:
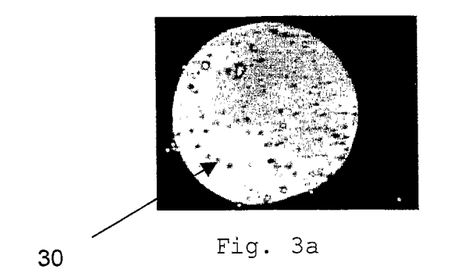
FIG. 3a and FIG. 3b are fluorescence images of a semiconductor nanostructure having immobilized morpholinos thereon.
Figure 3B:
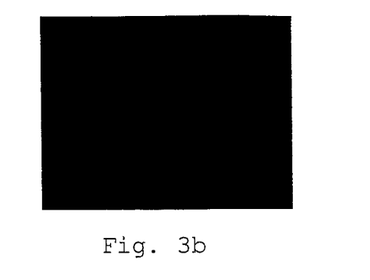

To assess the ability of morpholino as nucleic acid detection probe, fully complementary DNA molecules labeled with Cy 3 (each having base sequence 5'-Cy3-TGAGGTAG-TAGGTTGTGTGGTT-3' (SEQ ID NO:2)) (1st BASE Oligos (Singapore)) were hybridized to the spotted morpholino of Example 1, and the hybridization event was imaged by fluorescence microscope. FIG. 3a is the fluorescence image of the silicon nanostructure after the morpholinos have hybridized with the target DNA molecules that had been labeled with a Cy-3 fluorescent marker. As observed in FIG. 3a, a strong fluorescence spot is visible as indicated by arrow 30, indicating that DNA was hybridized only to the spotted area, which is covered with morpholino. Denaturation was then performed by placing the silicon nanostructure surface in an 8.3 M urea (Sigma-Aldrich) solution at room temperature for 5 minutes followed by a rinse with water. FIG. 3b is the fluorescence image after the target DNA molecules of FIG. 3a have been denatured and hence removed from the morpholinos. FIG. 3b shows that there are hardly any fluorescence spots in the image, demonstrating the efficient removal of the target DNA molecules from the silicon nanostructure and hence, the possibility of reusing the silicon nanostructure for further hybridization after the hybridized target nucleic acids had been removed.

The hybridization of the DNA molecules to the silicon nanostructure such as silicon nanowire (SiNW) can be detected via measuring the change in resistance between two terminal electrodes of the silicon nanostructure before and after hybridization. Here, the SiNW resistances are measured between the two terminals, source (S) and drain (D) electrodes with Alessi REL-6100 probe station (Cascade Microtech, Beaverton, Oreg.). The resistance change before and after hybridization of the DNA molecules to the morpholino probes is caused by the introduction of negatively charged DNA since the morpholino probe has a substantially non-ionic backbone and is hence, neutral. Hybridization was done in 1×SSC buffer and the electrical measurement was carried out in 0.01×SSC buffer. An acrylic reservoir is used to allow for fluid exchange for hybridization and measurement experiments. Fluid supply and return were carried out by Tygon tubes. A different SiNW chip was used for each individual measurement. At least 15 wires were measured each time and the mean of the resistance is utilized for data analysis.

Example 3

Figure 4:
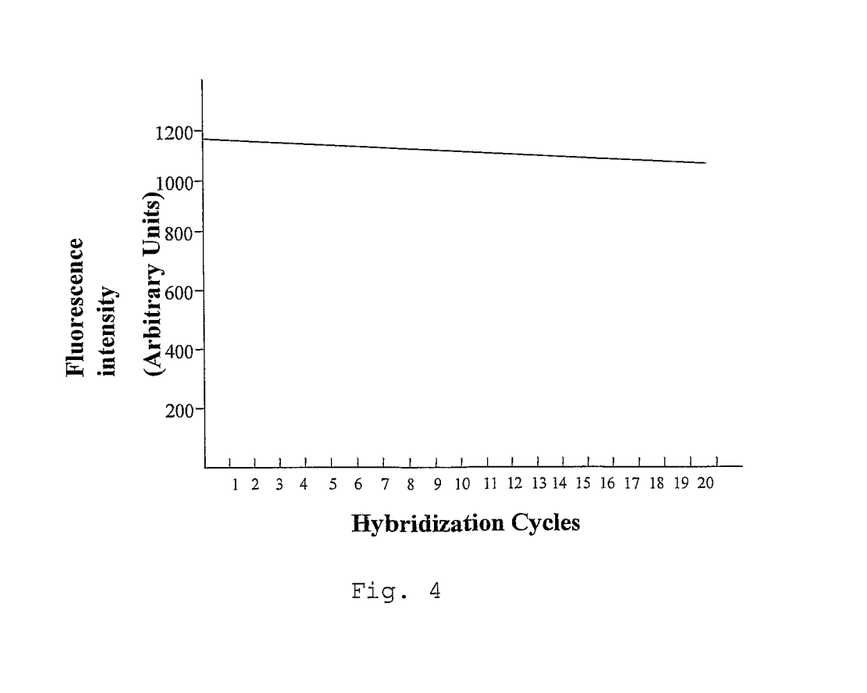
FIG. 4 is a graph showing the stability of the morpholinos-immobilized silicon surface after 20 cycles of hybridization and denaturation.

To investigate the stability of Morpholinos-modified silicon surface, the spotted area of FIG. 3a was used for repeated hybridization by denaturing fully complementary Morpholinos-DNA duplex and re-hybridizing the same Cy 3 labeled DNA to the Morpholinos-modified surface. Referring to FIG. 4, there is shown a graph of the stability of the morpholinos-immobilized silicon surface after 20 cycles of hybridization and denaturation. FIG. 4 demonstrates that repeated hybridization-denaturation cycles do not substantially affect the sensitivity of the immobilized morpholino probes. The fluorescence intensity after 20 cycles is ~90% of the initial value, corresponding to a loss of 0.5% per cycle, indicating the high reusability potential of a Morpholino-based nucleic acid microarray sensor.

Example 4

To assess the ability of PNA as another candidate for the neutral charged nucleic acid detection probe, PNA probe having a base sequence of 5'-$NH_2$-AACCACACAACCTAC-TACCTCA-3' (SEQ ID NO:3) (Eurogentec (Seraing, Belgium)) is immobilized to SiNW using the method of Example 1. The hybridization of either fully matched target DNA (with base sequence 5'-TGAGGTAGTAGGTTGTGTGGTT-3' (SEQ ID NO:4)) or one-base mismatch target DNA (with base sequence 5'-TGAGGTAGTAGGATGTGTGGTT-3' (SEQ ID NO:5)) (1st BASE Oligos (Singapore)) or non-complementary DNA (with base sequence 5'-ATGCATG-CATGCATGCATGCAA-3' (SEQ ID NO:6)) to PNA probe is detected using electrical measurements. Similar to the electrical measurement performed with Morpholino probe, the SiNW resistances upon binding of target DNA to probe PNA are measured between the two terminals, source (S) and drain (D) electrodes with Alessi REL-6100 probe station (Cascade Microtech, Beaverton, Oreg.). The resistance change before and after hybridization of the DNA molecules to the PNA probes is caused by the introduction of negatively charged DNA since the PNA probe has a substantially non-ionic backbone and is hence, neutral. Hybridization was done in 1×SSC buffer and the electrical measurement was carried out in 0.01×SSC buffer. An acrylic reservoir is used to allow for fluid exchange for hybridization and measurement experiments. Fluid supply and return were carried out by Tygon tubes. A different SiNW chip was used for each individual measurement. At least 15 wires were measured each time and the mean of the resistance is utilized for data analysis.

Figure 5:
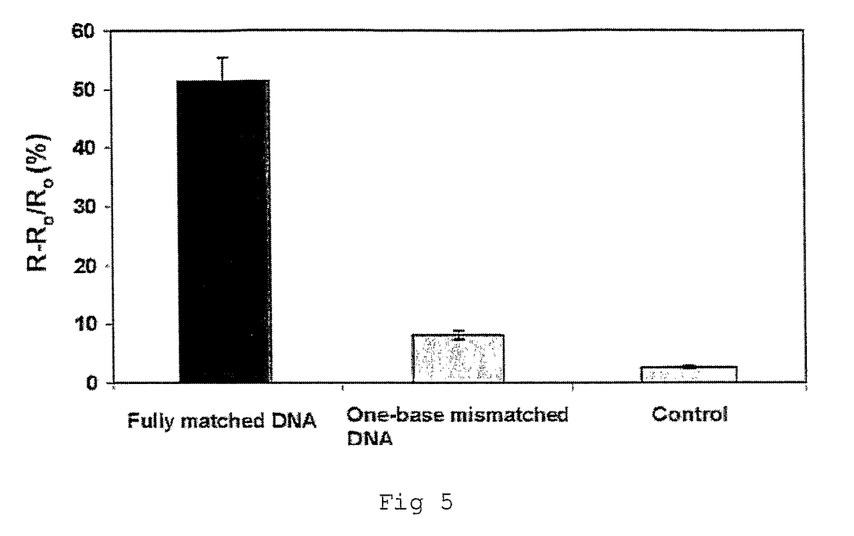
FIG. 5 is a graph showing the PNA modified SiNW biosensor response to complementary, one-base pair mismatch and non-complementary PNA-DNA hybridization.

Referring to FIG. 5, there is shown a graph depicting the change in resistance of electrical current flowing between the PNA-modified SiNW upon incubation with either fully matched, or one-based mismatched or non-complementary DNA. Incubation of the fully matched DNA to the PNA-modified SiNW results in a 51% increase in resistance change while incubation of non-complementary or one-base mismatched DNA results in negligible change in resistance. The results indicating the strong potential of PNA to be used as neutral charge nucleic acid probe for SiNW biosensor applications.

APPLICATIONS

The disclosed sensor can be used in a DNA microarray or in a gene chip such as a "lab-on-a chip" to determine the expression profiles of many genes at the same time. The disclosed sensor can be used in the fields of molecular biology and medicine for basic research, disease diagnostics and drug discovery.

The disclosed sensor can detect the hybridization of target nucleic acids using a fluorescence detection method and/or an electrical detection method that does not include optical detection (thereby saving on complex optical detection systems). Accordingly, the disclosed sensor may be more versatile than conventional sensors, which use fluorescence detection methods because the disclosed sensor can employ more than one detection method to determine hybridization of target nucleic acids.

The disclosed sensor or nucleic acid microarray can be re-used and can go through a number of hybridization-denaturation cycles without a substantial decrease in the sensitivity of the nucleic acid detection probes. This is compared to conventional microarrays where the fluorescence signal of the hybridized nucleic acids decreases by around 30% to 50% after three or more rounds of denaturation and re-hybridization, indicating a loss in the sensitivity of the detection probes.

The disclosed sensor can be used to detect a number of nucleic acid sequences that are different from each other. The target sequence moiety of the second polymer can be changed as required in order to hybridize target nucleic acids having different nucleic acid sequences. Hence, the sensor can be used for a number of applications. This permits the development of a universal hybridization assay, which can be used for testing samples under similar experimental conditions. Therefore, this may permit the comparison of data from different experimental sets, leading to increased reliability because the different experimental sets are carried out under similar experimental conditions.

The disclosed sensor does not require the use of DNA analogs as the detection probe. Instead, a polymer having a substantially non-ionic backbone is used as the detection probe in the sensor. When morpholino is used as the polymer, the morpholino imparts certain properties such as stability, nuclease-resistance, high efficacy, long-term activity, low-toxicity and high level of specificity to the sensor. Morpholinos are also cost-effective, which will reduce the cost involved with producing the disclosed sensor, particularly compared to sensors, which employ PNA. In addition, rigid backbone of morpholino allows easy access of target molecules compared with flexible backbone of DNA and PNA, which does not stand vertically on a surface, thus hampering the approach of target molecules, thereby reducing hybridization efficiency.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A sensor for detection of a target nucleic acid comprising:
   (a) a semiconductor nanostructure;
   (b) a polymer having a substantially non-ionic backbone linked to the semiconductor nanostructure; and
   (c) a nucleic acid detection probe having a substantially non-ionic backbone that hybridizes with the target nucleic acid, said nucleic acid detection probe comprising a first domain comprising a sequence complementary to the polymer and a second domain comprising a sequence complementary to the target nucleic acid, wherein said nucleic acid detection probe is not immobilized to the semiconductor structure.

2. The sensor of claim 1, wherein each of the polymer and the nucleic acid detection probe is at least one of peptide nucleic acid and morpholine.

3. The sensor of claim 1, wherein the second domain of the nucleic acid detection probe comprises a target sequence moiety that is selected to hybridizes with said target nucleic acid via complementary base pairing.

4. The sensor of claim 1, wherein said semiconductor nanostructure is selected form the group consisting of a Group IIIA-Group VA semiconductor, a Group IIB-Group VIA semiconductor, a Group IIA-Group VIA semiconductor, a Group IVA-Group VIA semiconductor, a Group IB-VIIA semiconductor, alloys and combinations thereof.

5. The sensor of claim 1, wherein said semiconductor nanostructure is selected form the group consisting of a semiconductor nanowire, a semiconductor nanotube and a semiconductor nanorod.

6. The sensor of claim 1, wherein said semiconductor nanostructure is comprised of a material selected from at least one of silicon and carbon.

7. The sensor of claim 1, wherein said target nucleic acid is a single stranded DNA molecule or a RNA molecule.

8. The sensor of claim 7, where said DNA molecule or said RNA molecule is labeled with a fluorescence marker.

9. A nucleic acid microarray sensor for detection of plural target nucleic acid sequences comprising:
a) a semiconductor nanostructure; and
b) an array of nucleic acid detection probes comprising
   (i) a polymer having a substantially non-ionic backbone linked to the semiconductor nanostructure; and
   (ii) a detection probe having a substantially non-ionic backbone and having a first domain comprising a target sequence moiety that hybridizes with said nucleic acid and a second domain complementary to the polymer and wherein the detection probe is not immobilized to the semiconductor nanostructure;
wherein different nucleic acid detection probes of said array are configured to hybridize with specific target nucleic acid sequences to thereby differentiate between said plural target nucleic acid sequences.

10. A system for detection of a target nucleic acid comprising:
a) a semiconductor nanostructure;
b) a polymer having a substantially non-ionic backbone and a binding moiety wherein the polymer is linked to the semiconductor nanostructure; and
c) a nucleic acid detection probe comprising a first domain that hybridizes with the target nucleic acid and a second domain comprising a binding moiety that binds to the binding moiety of the polymer, said nucleic acid detection probe having a substantially non-ionic backbone and wherein the nucleic acid detection probe is no immobilized to the semiconductor nanostructure; and
c) a detection system for detecting the hybridization between said target nucleic acid and said detection probe.

11. A method for detection of a target nucleic acid comprising the steps of:
providing a sensor of claim 1 and contacting the sensor with a sample comprising a target nucleic acid under conditions to allow the target nucleic acid and the nucleic acid detection probe to hybridize and detecting an electromagnetic field change in said semiconductor nanostructure that is indicative of hybridizing between said target nucleic acid and said nucleic acid detection probe.

12. The method of claim 11, further comprising, before said providing step, the steps of:
functionalizing said semiconductor nanostructure surface with amine groups; and
covalently attaching said polymer to the amine functionalized semiconductor nanostructure surface.

13. The method of claim 12, wherein said functionalizing step comprises the step of using an amino-group containing compound as a functionalizing agent.

14. The method of claim 13, wherein said amino-group containing compound is 10-aminodec-1-ene.

15. The method of claim 12, wherein said attaching step comprises the step of using a cross-linker to covalently attach said polymer to said nanostructure surface.

16. The method of claim 15, wherein said cross-linker is an organic compound having an oxo group at both terminal ends.

17. The method of claim 16, wherein said organic compound having an oxo group is glutaraldehyde or phenylene diisocyanate.

18. A kit for detection of a target nucleic acid comprising:
a) a semiconductor nanostructure;
b) a polymer having a substantially non-ionic backbone linked to the semiconductor nanostructure;
c) nucleic acid detection probe having a substantially non-ionic backbone that hybridizes with the target nucleic acid, said nucleic acid detection probe comprising a first domain comprising a sequence complementary to the polymer and a second domain comprising a sequence complementary to the target nucleic acid; and
c) a detection system for detecting the hybridization between said target nucleic acid and said detection probe.

19. The kit of claim 18, wherein said detection system is selected from the group consisting of a fluorescence reader, an ammeter, a voltmeter and an ohm meter.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: morpholino

<400> SEQUENCE: 1
aaccacacaa cctactacct ca                                          22

<210> SEQ ID NO 2
<211> LENGTH: 22
<212> TYPE: DNA
```

```
<213> ORGANISM: Artificial Sequence
<220> FEATURE:
<223> OTHER INFORMATION: Target DNA of Example 2

<400> SEQUENCE: 2
tgaggtagta ggttgtgtgg tt                                              22

<210> SEQ ID NO 3
<211> LENGTH: 22
<212> TYPE: DNA
<213> ORGANISM: Artificial Sequence
<220> FEATURE:
<223> OTHER INFORMATION: PNA probe

<400> SEQUENCE: 3
aaccacacaa cctactacct ca                                              22

<210> SEQ ID NO 4
<211> LENGTH: 22
<212> TYPE: DNA
<213> ORGANISM: Artificial Sequence
<220> FEATURE:
<223> OTHER INFORMATION: Fully matched target DNA of Example 4

<400> SEQUENCE: 4
tgaggtagta ggttgtgtgg tt                                              22

<210> SEQ ID NO 5
<211> LENGTH: 22
<212> TYPE: DNA
<213> ORGANISM: Artificial Sequence
<220> FEATURE:
<223> OTHER INFORMATION: One-base mismatch target DNA of Example 4

<400> SEQUENCE: 5
tgaggtagta ggatgtgtgg tt                                              22

<210> SEQ ID NO 6
<211> LENGTH: 22
<212> TYPE: DNA
<213> ORGANISM: Artificial Sequence
<220> FEATURE:
<223> OTHER INFORMATION: Non-complementary DNA of Example 4

<400> SEQUENCE: 6
atgcatgcat gcatgcatgc aa                                              22
```